United States Patent [19]

Creighton

[11] Patent Number: 4,977,248

[45] Date of Patent: Dec. 11, 1990

[54] PROCESS FOR THE PRODUCTION OF A PROTEIN

[76] Inventor: Thomas E. Creighton, Caxton Cottage, Swaffham Prior, Cambridge, England, CB5 0HT

[21] Appl. No.: 391,709

[22] Filed: Aug. 10, 1989

Related U.S. Application Data

[63] Continuation of Ser. No. 939,043, filed as PCT GB86/00188 on Apr. 1, 1986, published as WO86/05809 on Oct. 9, 1986, abandoned.

[30] Foreign Application Priority Data

Mar. 29, 1985 [GB] United Kingdom ............... 8508340

[51] Int. Cl.$^5$ ........................................... C07K 3/20
[52] U.S. Cl. ................................. 530/412; 530/413; 530/415; 530/416; 530/417; 530/820; 530/408; 530/409; 530/410; 435/69.1; 435/69.7
[58] Field of Search ...................... 530/412–413, 530/415, 416, 417, 820, 408–410; 435/69.1, 69.7

[56] References Cited

U.S. PATENT DOCUMENTS

| | | | |
|---|---|---|---|
| 4,568,488 | 2/1986 | Lee-Huang | 424/85 |
| 4,572,798 | 2/1986 | Koths et al. | 530/351 |
| 4,656,255 | 4/1987 | Seely | 530/412 |
| 4,659,568 | 4/1987 | Heilman | 530/417 |
| 4,766,205 | 8/1988 | Rausch | 530/412 |
| 4,766,224 | 8/1988 | Ghosh-Dastidar | 530/412 |
| 4,839,419 | 6/1989 | Kraemer et al. | 530/412 |

FOREIGN PATENT DOCUMENTS 0114506  8/1984  European Pat. Off. .

OTHER PUBLICATIONS

Orsini et al, JBC 253, 1978, pp. 3453–3458.
Odorzynski et al., JBC 254, 1979, pp. 4291–4295.
Light, Bio Techniques, vol. 3(4), 1985, pp. 298–306.
Sofer et al, Bio Techniques, 1983 (Nov./Dec.), pp. 198–203.

Primary Examiner—Garnette Draper
Attorney, Agent, or Firm—Cushman, Darby & Cushman

[57] ABSTRACT

A method for the renaturation of unfolded proteins comprises reversibly immobilizing the denatured protein on a solid phase and inducing folding of the immobilized protein by progressively reducing with time the concentration of a denaturing agent in the solvent in contact with the solid phase. The refolded protein is recovered from the solid phase in native form. The proteins can be folded and recovered in high yield in a small volume of buffer.

12 Claims, 6 Drawing Sheets

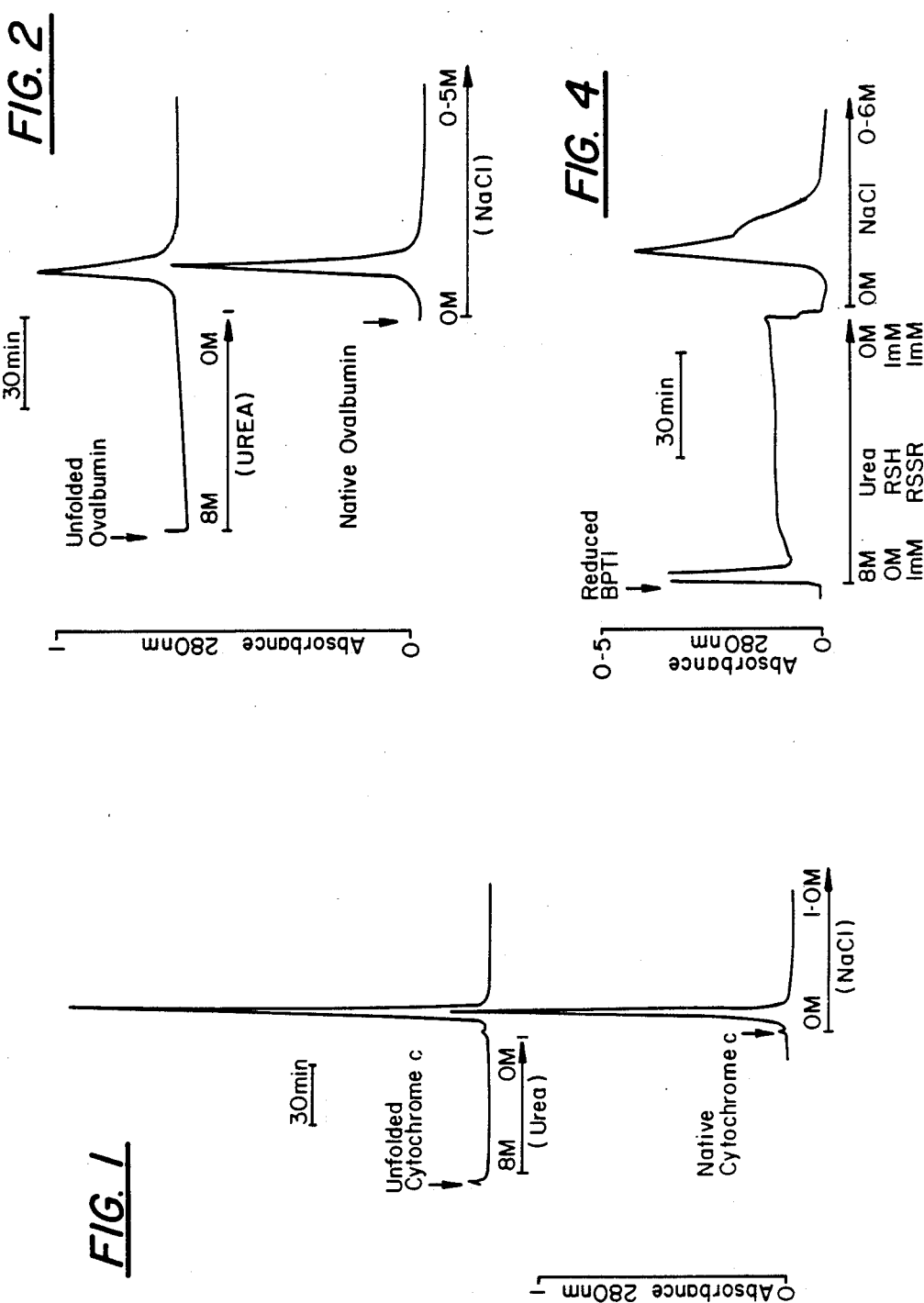

PROCESS FOR THE PRODUCTION OF A PROTEIN

This is a continuation of application Ser. No. 06/939,043 filed as PCT GB86/00188 on Apr. 1, 1986, published as WO86/05809 on Oct. 9, 1986 which was abandoned upon the filing hereof.

This invention relates to processes for the production of proteins, in particular to the production of soluble native proteins. Especially the invention relates to a process for the production of a soluble native protein, in which an insoluble form of the protein is produced by host cells transformed with a vector including a gene coding for the protein, and as such relates to the field of protein production using recombinant DNA biotechnology.

A protein exists as a chain of amino acids linked by peptide bonds. In the normal biologically active form of a protein (hereinafter referred to as the native form) the chain is folded into a thermodynamically preferred three dimensional structure, the conformation of which is maintained by relatively weak interatomic forces such as hydrogen bonding, hydrophobic interactions and charge interactions. Covalent bonds between sulphur atoms may form intramolecular disulphide bridges in the polypeptide chain, as well as intermolecular disulphide bridges between separate polypeptide chains of multisubunit proteins, e.g. insulin.

There are now numerous examples of commercially valuable proteins which may be produced in large quantities by culturing host cells capable of expressing heterologous genetic material, i.e. using the techniques of recombinant DNA biotechnology. However in some cases, in particular when proteins are produced in *E. coli* host cells, the proteins are produced within the host cells in the form of insoluble protein aggregates and in this form do not exhibit the functional activity of their natural counterparts and are therefore in general of little use as commercial products. The lack of functional activity may be due to a number of factors but it is likely that such proteins produced by transformed cells are formed in a conformation which differs from that of their native form. They may also possess unwanted intermolecular disulphide bonds not required for functional activity of the native protein in addition to intramolecular disulphide bonds. The altered three dimensional structures of such proteins not only leads to insolubility but also diminishes or abolishes the biological activity of the protein.

In order to produce such proteins in a native, biologically active form the insoluble protein aggregates have been solubilised with denaturants. The resultant solution containing the denatured protein with the individual polypeptide chains unfolded is then treated to remove the denaturant or otherwise reverse the denaturing conditions and thereby permit renaturation of the protein and folding of the polypeptide chains in solution to give protein in native, biologically active form. Published International Patent Application No. WO 83/04418 describes such a procedure for the production of chymosin precursor proteins in a form capable of being converted to active chymosin.

However, the usual insolubility under folding conditions of fully—or partially—unfolded proteins requires that folding be carried out in very dilute solutions, and in large volumes. The handling of such dilute solutions and large volumes can add significantly to the cost when such processes are applied industrially.

I have now found that unfolded proteins may be adsorbed reversibly on solid phase adsorbents, induced to fold whilst bound to the adsorbent by progressively reducing with time the concentration of denaturing agent in the solvent in contact with the adsorbent, and then eluted from the adsorbent to yield the protein in native form. This provides a process for the production of soluble native proteins which avoids the requirement for refolding of the protein in very dilute solution, and in large volumes, and thus provides benefits for industrial scale applications. The process further provides a way of separating different proteins or different conformational states. Other advantages and benefits of this process are described hereinafter and will be apparent to those skilled in the art of protein production. The process may be applied advantageously to proteins produced by recombinant DNA biotechnology which are produced within host cells in the form of insoluble protein aggregates.

BRIEF DESCRIPTION OF THE DRAWINGS

FIG. 1 is a graph showing the refolding of horse cytochrome c adsorbed to CM-cellulose.

FIG. 2 is a graph showing the refolding of hen ovalbumin adsorbed to DEAE-cellulose.

Figure 3A:
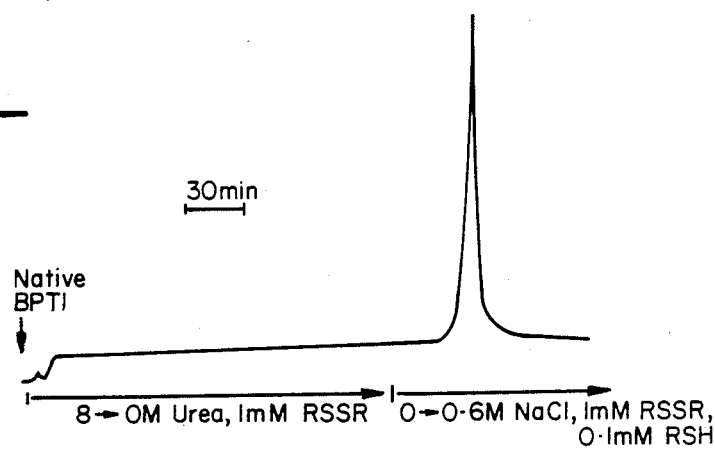
FIG. 3 is a graph showing the refolding of reduced bovine pancreatic trypsin inhibitor (BPTI) adsorbed to CM-cellulose.

Accordingly the present invention comprises a process for the production of a protein in native form, in which a solution of the denatured protein is contacted with a solid phase which reversibly binds the protein and the denatured protein is reversibly bound to the solid phase, characterised in that, the bound protein is renatured by progressively reducing with time the concentration of the denaturing agent in the solvent in contact with the solid phase, and the renatured protein is recovered from the solid phase in native form.

The process of the invention may be applied to any protein which is produced in a non-native form e.g. in the form of insoluble protein aggregates. The process may be used to convert the non-native form of the protein to the native form, e.g. the soluble native form of the protein. In particular the invention may be applied to proteins produced by recombinant DNA biotechnology, in which an insoluble form of the protein is produced by host cells transformed with a vector including a gene coding for the protein. Examples of 'recombinant' proteins produced in insoluble form by transformed host cells are porcine growth hormone, tissue inhibitor of metalloproteinases (TIMP), insoluble chymosin precursors e.g. met-prochymosin, immunoglobulins and CAT-fusion proteins e.g. CAT-calcitonin, produced in bacteria (e.g. *E. coli*) or yeast (e.g. *S. cerevisiae*) host cells.

The protein may be denatured in any suitable denaturant solution. The solution of the denaturing agent may be chosen having regard to the solid phase to be used for reversible binding of the denatured protein. The denaturing agent may be in aqueous solution, such as for example an aqueous solution of guanidine hydrochloride, though is preferably urea, e.g. 8M urea.

The solid phase may be any solid phase to which the denatured protein may be reversibly bound. The protein may be bound to the solid phase by reversible covalent linkage. Alternatively the solid phase may comprise an adsorbent for the protein. For instance the solid phase may be an ion-exchange resin such as an agarose or similar material e.g. Q-sepharose or S-sepharose, Pharmacia Mono Q FPLC, Pharmacia Mono S FPLC, or cellulose, e.g. CM-cellulose, DEAE-cellulose, phospho-cellulose, or Amberlite of which CM-cellulose and Pharmacia Mono Q FPLC are preferred. It will be appreciated that when the solid phase is an ion-exchange resin the denaturant solution used is typically of low ionic strength to promote adsorption of the protein.

The solid phase may comprise a continuous solid phase such as a surface, though is preferably particulate. Advantageously the solid phase may be in the form of a column containing particles of the solid phase through which the denaturant solution and solvent may be flowed.

Renaturing of the protein bound to the solid phase is effected by progressively reducing with time the concentration of denaturing agent in the solvent in contact with solid phase to which the protein is bound. In a preferred embodiment the protein bound to the solid phase is treated with a solvent gradient, preferably a linear gradient, in which the composition varies from one in which the solvent initially presents a denaturing environment to one in which the solvent presents a natural environment to the protein. For example a urea gradient varying from an initial urea concentration of 8M to a final concentration of 0M may be used. The composition of the gradient is typically varied in a continuous manner, e.g. linearly, over a prolonged period of time, usually at least over about 30 minutes and preferably over about 60 minutes. Preferably the solvent gradient is passed through a column containing bound protein.

In addition to denaturant the solvent which is contacted with the solid phase may contain other components such as cofactors, disulphide forming and breaking reagents and salts. The concentrations of these other components may be varied as desired during renaturation of the protein.

On completion of renaturation treatment the protein is recovered from the solid phase. For instance renatured protein may be recovered from an ion-exchange resin column by elution with a salt, e.g. NaCl, gradient.

The invention also extends to a protein whenever produced by the process according to the invention.

The invention is further described by way of illustration only in the following examples. It will be appreciated that the results presented in the examples demonstrate the feasibility of the process of the invention for production of proteins in general in native form.

EXAMPLE 1

This Example relates to studies of model proteins.

MATERIALS AND METHODS

Proteins

Horse cytochrome c was obtained from BDH. Hen ovalbumin was obtained from Sigma. Bovine pancreatic trypsin inhibitor (BPTI, R Trasylol) was the generous gift of Bayer AG.

Ion Exchange Resins

The carboxymethyl-(CM) and diethylaminoethyl-(DEAE) cellulose resins were respectively the CM52 and DE52 products of Whatman.

Unfolding of Proteins

Proteins were unfolded by dissolving the dry native protein obtained commcercially to a concentration of 5 to 10 mg/ml in 8M urea also containing the appropriate buffer. Unfolding of ovalbumin was ensured by heating the solutions at 50° for 15 minutes. When disulphides were also to be reduced, dithiothreitol was included at 50 mM. Urea was the Aristar grade of BDH, and all urea solutions were prepared just prior to use.

Solid-state refolding of proteins

Small columns of the appropriate resin (generally 1.5 cm in diameter and 3 cm in length) were equilibrated with the desired buffer in which the protein was determined to adsorb tightly. Most frequently, this was 10 to 100 mM Tris-HCl at pH 8.7 with 1 mM EDTA. Just before applying the unfolded protein, the column was washed with a few ml of the same buffer solution containing 8M urea. Usually 10 to 20 mg of unfolded protein in 2 ml of 8M urea was applied to the column. It was followed by the buffers designed to induce the adsorbed protein to fold, usually using a linear gradient to remove gradually the urea and to vary other parameters. The protein was then eluted with an appropriate salt gradient and the elution profile compared with that of the same amount of protein that had not been unfolded. The flow rates varied between 1.0 and 3.3 ml/min.

The absorbance at 280 nm of the eluate was monitored continuously, and fractions of 200 drops (about 13 ml) collected. Thiols were assayed by the method of Ellman (Arch. Biochem. Biophys 82:70 (1959)) and active BPTI by its ability to inhibit trypsin (Kassell B., Methods Enzymol 19, 844 (1970)). Assays were performed at 25°, all other manipulations were at room temperature.

a. Horse Cytochrome c

Horse cytochrome c (FIG. 1) was unfolded in 8M urea (Myer Y. P., Biochemistry 7 765 (1968); Stellwagen E., Biochemistry 7 289 (1968)) and applied to a small column of CM-cellulose at low ionic strength, where it was observed from its colour to bind to the top 1 to 2 mm of resin. The urea concentration of the solvent was gradually lowered by a linear gradient of 8M to 0M urea. The adsorbed protein was then quantitatively eluted with a gradient of increasing salt concentration. No coloured protein was retained by the column and the elution profile was indistinguishable from that of cytochrome c that had not been unfolded. The same result was obtained if the unfolded cytochrome c was dispersed by stirring it into the resin of the top third of the column.

If the urea was not removed gradually with a gradient, but omitted entirely from buffer applied to the column after the unfolded protein, only approximately 80% of the protein was eluted; the remainder was retained at the top of the column. Further experimental details are described below in the legend to FIG. 1.

FIG. 1. Refolding of horse cytochrome c adsorbed to CM-cellulose. The buffer throughout was 0.1M Tris-HCl, pH 8.7, 1 mM EDTA. 10.0 mg of cytochrome c dissolved in 1.0 ml of buffer (native, or unfolded with 8M urea also present) was applied to a column of CM-cellulose equilibrated with the same buffer. The unfolded protein was followed by a 200-ml linear gradient of 8M to 0M urea in buffer. Both proteins were eluted with a 200 ml linear gradient of 0M to 1.0M NaCl. The elution profile shown is given by the absorbance at 280 nm.

b. Ovalbumin

Unfolded ovalbumin is well-known to precipitate to a large extent upon removal of denaturant (Simpson et al, J. Amer. Chem. Soc. 75 5139 (1953)). The protein is usually heterogeneous, due to partial phosphorylation of two residues and the proteolytic cleavage, and the major doubly-phosphorylated species has been shown to unfold reversibly (Ahmad and Salahuddin, Biochemistry 15 5168 (1976)). When heterogeneous commercial ovalbumin was refolded while adsorbed to DEAE-cellulose, using a procedure like that employed with cytochrome c, a yield of approximately 50% of apparently refolded molecules was obtained (FIG. 2). Further experimental details are described below in the legend to FIG. 2.

FIG. 2. Refolding of hen ovalbumin adsorbed to DEAE-cellulose. The buffer throughout was 20 mM Tris-HCl, pH 8.7. 20 mg of ovalbumin dissolved in 2.0 ml of buffer (native, or unfolded with 8M urea also present) was applied to a column of DEAE-cellulose equilibrated with the same buffer. The unfolded protein was followed by a 200 ml linear gradient of 8M to 0M urea. Both proteins were eluted with a 200 ml linear gradient of 0M to 0.5M NaCl.

c. Bovine pancreatic trypsin inhibitor

Some proteins must form disulphides to attain a stable folded conformation, and this permits further manipulation and elucidation of the folding process. The protein best characterised in this respect is BPTI, with three disulphide bonds. Reduced BPTI protein in 8M urea and 50 mM dithiothreitol was applied to CM-cellulose columns; the urea concentration was gradually diminished with a linear gradient coupled to various alterations of the thiol/disulphide redox potential via the concentrations of the thiol and disulphide forms of glutathione, mercaptoethanol, or cysteamine, respectively negatively charged, neutral and positively charged. The protein was then eluted with a salt gradient (FIG. 3).

The absorbance at 280 nm detected both protein and the disulphide reagent; thiols and BPTI trypsin inhibitor activity were assayed in the eluant. These procedures measured the reactivity of the thiols with the disulphide reagent (to generate reduced reagent) and the proportion of eluted protein that had a native-like conformation.

At least 90% of the BPTI could be eluted from the column after removing the urea from the buffer by a linear gradient, which also included thiol and disulfide forms of mercaptoethanol, RSH and RSSR respectively, in constant, increasing, or decreasing concentrations. The disulphide reagent was included to generate protein disulphides, the thiol reagent to assist in protein disulphide rearrangements.

Figure 3B:
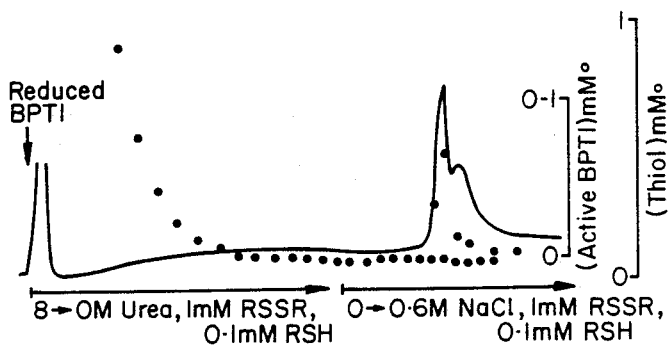
Figure 3C:
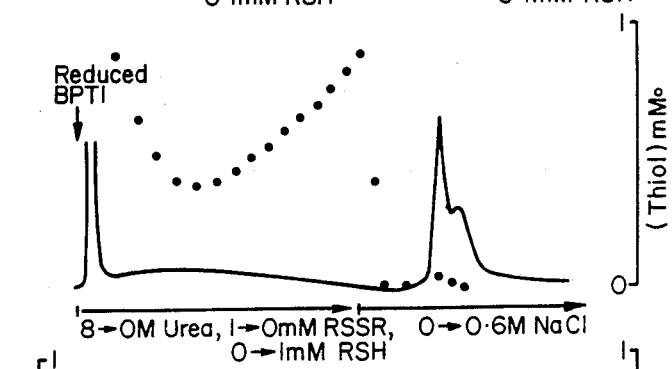
Figure 3D:
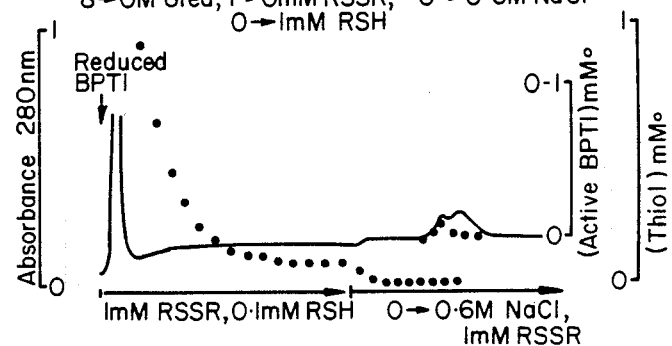

There was little dependence of the product on the type of RSH/RSSR gradient (FIG. 3b, c). However, it was necessary to have a gradient of decreasing urea concentration; an abrupt removal of the urea resulted in recovery of only a small fraction of the BPTI, and the inactive form predominated (FIG. 3d). Significantly higher yields of correctly folded BPTI were generated using a higher ionic strength buffer throughout (FIG. 4), where the protein would be expected to be less tightly adsorbed to the resin.

Further experimental details are provided in the legends to FIGS. 3 and 4.

FIG. 3. Refolding of reduced BPTI adsorbed to CM-cellulose. In each case, 20 mg of BPTI in 2 ml of 8M urea plus buffer was adsorbed. A is the control in which the BPTI was not reduced, but only dissolved in 8M urea, where it remains folded and the disulphides intact; B, C and D used reduced BPTI by inclusion of 50 mM dithiothreitol, which is the absorbing material not bound to the column. In A, B, and C, the protein was followed by a 200 ml linear gradient of 8M to 0M urea in buffer; in D there was no urea in the subsequent buffer and no gradient. 1.0 mM hydroxyethyl disulfide (RSSR) was present uniformly in the gradient buffers in A, B, and D; in C it was present only in the 8M urea solution and consequently decreased in concentration. Mercaptoethanol (RSH) was present uniformly at 0.1 mM in B and D, but in C was present at 1.0 mM in the 0M urea solution only and consequently increased in concentration. The proteins were eluted with 200 ml linear gradients of 0M to 0.6M NaCl in buffer. In A and B these solutions also contained 1.0 mM RSSR and 0.1 mM RSH; in D only 1 mM RSSR.

The buffer throughout was 10 mM Tris (pH 8.7) and 1 mM EDTA. The solid line gives the absorbance at 280 nm, which monitors both RSSR and protein.

FIG. 4. Improved yield of correctly refolded BPTI using 0.1M Tris-HCl, pH 8.7, 1 mM EDTA buffer throughout. The conditions were as in FIG. 3c, except for the ten-fold higher Tris concentration; also 1.0 mM RSSR was present uniformly throughout the urea gradient, whereas the concentration of RSH increased linearly from 0M to 1.0 mM.

Protein not eluted from the column may be recovered by going through a second treatment involving 8M urea and 50 mM dithiothreitol, followed by the refolding and disulphide formation steps.

A wide variety of solid supports may be used. Various hydrophilic ion-exchange resins were used here because of their availability and widespread use in chromatography of proteins, but there are very many other chromatographic supports that might be suitable. The electrostatic binding of the protein to the resin is not expected to interfere greatly with folding, since modification of the ionized groups of at least some proteins does not alter substantially their folding or stability. Globular proteins generally have all ionic groups on their surface. Non polar supports would be expected to interfere with the hydrophobic interaction that is important for folding of globular proteins, but might be ideal for membrane proteins.

The solvents used must be compatible with both adsorption of the protein to the solid support and variation of the folding conditions. Other parameters beside denaturant concentrations may be used to vary the folding conditions, such as temperature, pH, ionic strength, disulphide formation or breakage and ligand concentrations. Specific cofactors may also be included in the solvent to vary the folding conditions.

The unfolded protein adsorbed to the ion-exchange resin is accessible to at least small reagents, as shown by the reactivity of the thiol groups of BPTI. Disulfide bond formation is one type of post-translational modification, so others might also be possible, such as glycosylation, γ-carboxylation and hydroxylations. This would require that the adsorbed protein be accessible to the necessary reagents and enzymes.

A procedure to minimize aggregation of the protein bound to the solid support may be to use one or a few covalent, but reversible, attachments of the protein to a solid support.

EXAMPLE 2

Prochymosin

The cells used in this experiment were *E. coli* HB101 cells carrying the plasmid pCT70 which contains the gene coding for prochymosin. A full description of this plasmid and its derivation is provided in British Patent No. 2100737B.

10 g wet weight cells (HB101/pCT70) were suspended in 30 ml 50 mM TrisCl pH 8.0, 1 mM EDTA, 50 mM NaCl and lysed by one pass through a French press at 1250 p.s.i. The lysate was centrifuged at 12000 Xg for 5 minutes at 4° C. The pellet was suspended in 30 ml H$_2$O and centrifuged as before. The washed pellet was then suspended in 8 ml 20 mM TrisCl pH 9.0, 1 mM EDTA, 8M urea and incubated for 30 minutes at 30° C.

Figure 5:
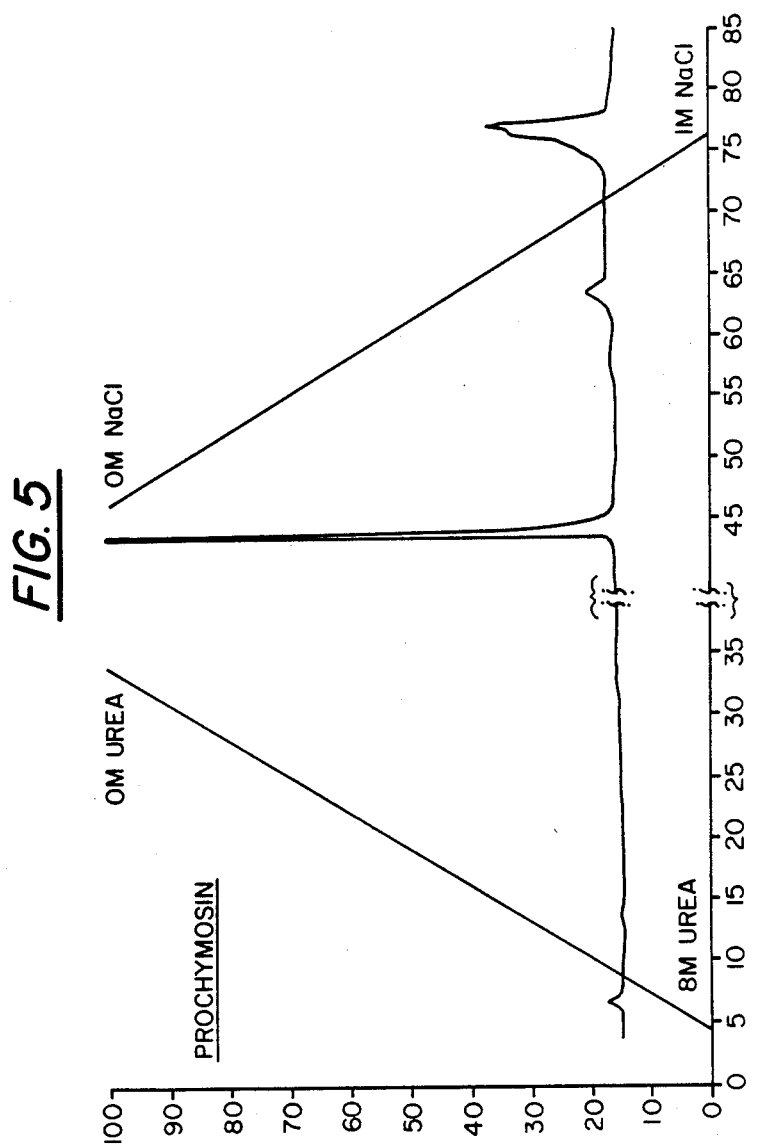
FIG. 5 is a graph showing the elution profile from a column carrying adsorbed prochymosin.

A 10 mm×100 mm Pharmacia Mono Q FPLC column was equilibrated with 20 mM ethanolamine pH 9, 8M urea. 200 μl of the prochymosin urea suspension was applied to the column at a flow rate of 0.5 ml.min$^{-1}$. A linear decreasing gradient of 8M to 0M urea in 20 mM ethanolamine pH 9.0 was applied to the column at a flow rate of 0.5 ml.min$^{-1}$ over a total period of 60 minutes. 1 ml fractions were collected. The column was then washed with 10 ml 20 mM ethanolamine pH 9.0 and developed with a linear gradient of 0M-1M NaCl in 20 mM ethanolamine pH 9.0 at a flow rate of 0.5 ml.min$^{-1}$ over a total period of 60 minutes. 1 ml fractions were collected. FIG. 5 shows the elution profile from this column, monitored at 280 nm.

Fractions collected from the column, as described below in the legends to FIGS. 6 and 7 were analysed by SDS Page on a 12.5% acrylamide gel run at 150 V for 4 hr according to the method of Laemmli (Nature 227 680–685 (1970)). The gel was stained with coomassie blue, destained in 7.5% acetic acid and then stained with silver stain (Merril et al, Science 211 1437 (1981)).

Figure 6:
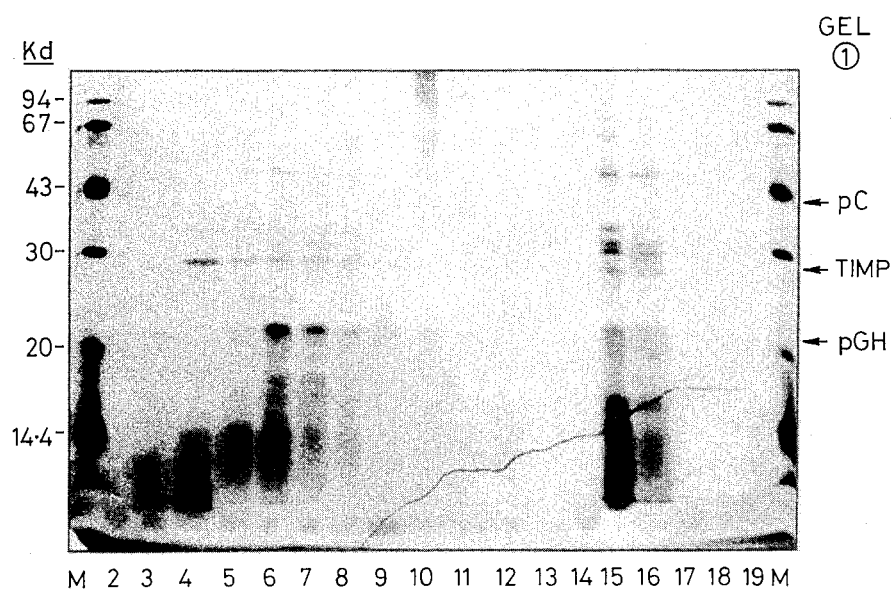
FIGS. 6 and 7 are reproductions of SDS-polyacrylamide gels showing fractions eluted from columns loaded with prochymosin, tissue inhibitor of metalloproteinases (TIMP) and porcine growth hormone (pGH).

| Track No. | FIG. 6 Sample | |
|---|---|---|
| 1 | Pharmacia Markers | |
| 2 | Fraction 66 | FPLC run - pGH |
| 3 | Fraction 67 | " |
| 4 | Fraction 68 | " |
| 5 | Fraction 70 | " |
| 6 | Fraction 71 | " |
| 7 | Fraction 72 | " |
| 8 | Fraction 73 | " |
| 9 | Fraction 74 | " |
| 10 | Fraction 75 | " |
| 11 | Fraction 76 | " |
| 12 | Fraction 77 | " |
| 13 | Fraction 34 | " |
| 14 | Fraction 37 | " |
| 15 | Fraction 43 | FPLC run - TIMP |

| Track No. | -continued FIG. 6 Sample | |
|---|---|---|
| 16 | Fraction 44 | " |
| 17 | Fraction 45 | " |
| 18 | Fraction 6 | FPLC run - Chymosin |
| 19 | Fraction 7 | " |
| 20 | Pharmacia Markers | |

Figure 7:
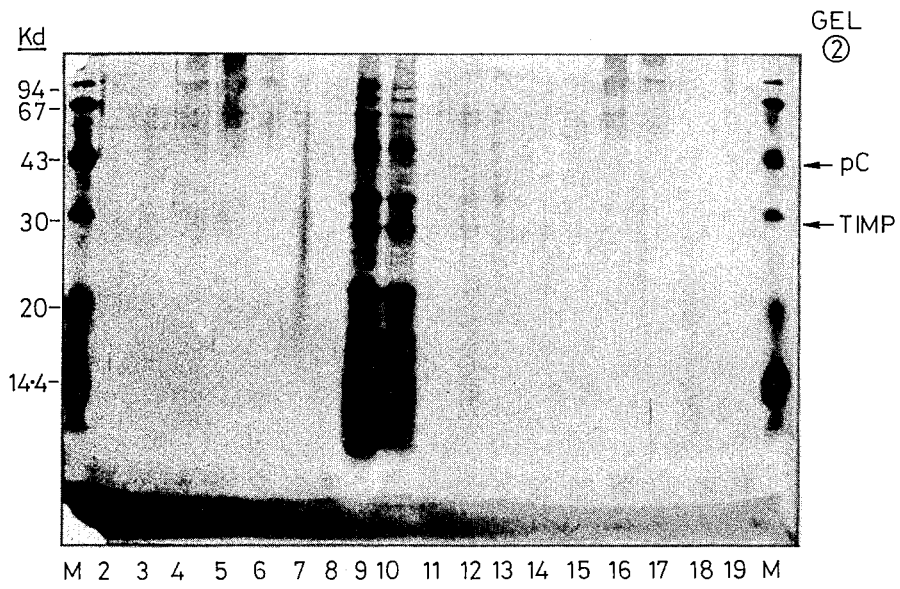

| Track No. | FIG. 7 Sample | |
|---|---|---|
| 1 | Pharmacia Markers | |
| 2 | Fraction 74 | FPLC run - TIMP |
| 3 | Fraction 75 | " |
| 4 | Fraction 76 | " |
| 5 | Fraction 77 | " |
| 6 | Fraction 78 | " |
| 7 | Fraction 40 | FPLC run- Chymosin |
| 8 | Fraction 41 | " |
| 9 | Fraction 43 | " |
| 10 | Fraction 44 | FPLC run - Chymosin |
| 11 | Fraction 62 | " |
| 12 | Fraction 63 | " |
| 13 | Fraction 64 | " |
| 14 | Fraction 74 | " |
| 15 | Fraction 75 | " |
| 16 | Fraction 76 | " |
| 17 | Fraction 77 | " |
| 18 | Fraction 78 | " |
| 19 | Fraction 79 | " |
| 20 | Pharmacia Markers | |

EXAMPLE 3

Tissue Inhibitor of Metalloproteinases (TIMP)

The cells used in this experiment were *E. coli* E103S cells carrying the plasmid pMG461 which contains the gene coding for TIMP. The derivation of plasmid pMG461 is described in our co-pending British patent application No. 8600199 filed Jan. 6, 1986.

The experiment was performed essentially as described in Example 2, using *E. coli* E103S cells carrying plasmid pMG461 in place of *E. coli* HB101 carrying plasmid pCT 70.

Figure 8:
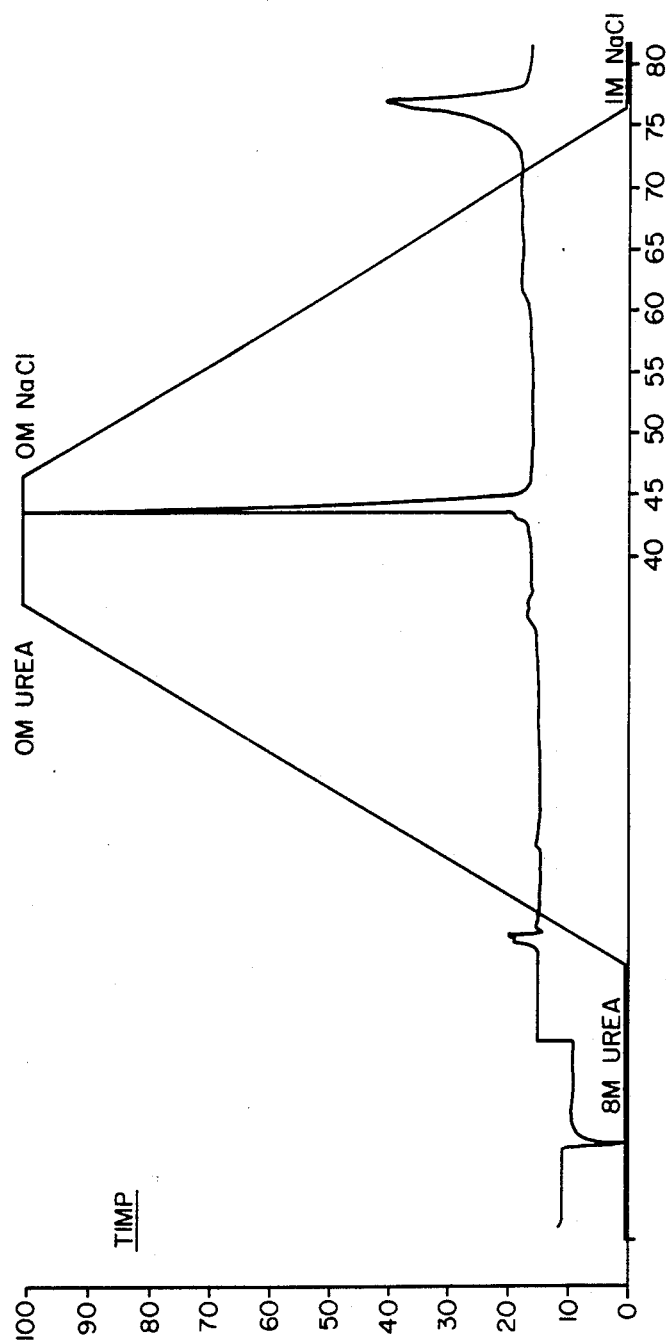
FIG. 8 is a graph showing the elution profile from a Pharmacia Mono Q FTLC column loaded with TIMP, monitored at 280 nm.

FIG. 8 shows the elution profile from the Pharmacia Mono Q FPLC column monitored at 280 nm.

Fractions collected from the column as described above in the legends to FIGS. 6 and 7 were analysed as described in Example 2.

EXAMPLE 4

Porcine Growth Hormone

The cells used in this experiment were *E. coli* E1035S carrying the plasmid pMG935. A gene coding for porcine growth hormone may be derived as described in published European patent applications Nos. EP 104920A (Biogen) and EP 111389A (Genentech).

Plasmid pMG935 is a derivative of pMG196, carrying the gene encoding porcine growth hormone. pMG196 is a dual-origin expression vector carrying the pTrp promoter and T$_7$ terminator. To construct pMG196 a XhoI-BamHI DNA fragment carrying the Col EI origin from pMG15 was ligated to an EcoRI BamHI DNA fragment isolated from pMG411 (Yarranton et al Gene 28 293–300 (1984)), and to an EcoRI-SalI DNA fragment carrying λpR and cI857 from pCQV2 (Queen J. Mol. and Applied Genet. 2 1–10 (1983)) which had a SalI-HindIII DNA linker inserted at the unique BamHI site of this plasmid. The resulting plasmid was cleaved with EcoRI and PstI and the DNA fragment carrying the pSC101 origin replaced with an EcoRI to PstI DNA fragment from pMG168, carrying a pSC101 origin and par function. This plasmid is pMG171. pMG171 was cleaved with BamHI and PstI and the small DNA fragment replaced with a BamHI-PstI fragment isolated from pCT54 (Emtage et al PNAS USA 80 (1983) 3671-3675). This fragment carried the pTrp and T7 terminator and the resulting plasmid is pMG196 (Wright et al submitted for publication). The gene for pGH was assembled into pMG196, by inserting into partially EcoRI cleaved, ClaI cleaved vector, and after ligation and transformation ampicillin resistant transformants were selected at 30° C. The plasmid isolated from these transformants is pMG935, and expresses pGH from the pTrp.

The experiment was carried out essentially as described in Example 2, using *E. coli* E103S carrying plasmid pMG935 in place of *E. coli* HB101 carrying plasmid pCT 70.

Figure 9:
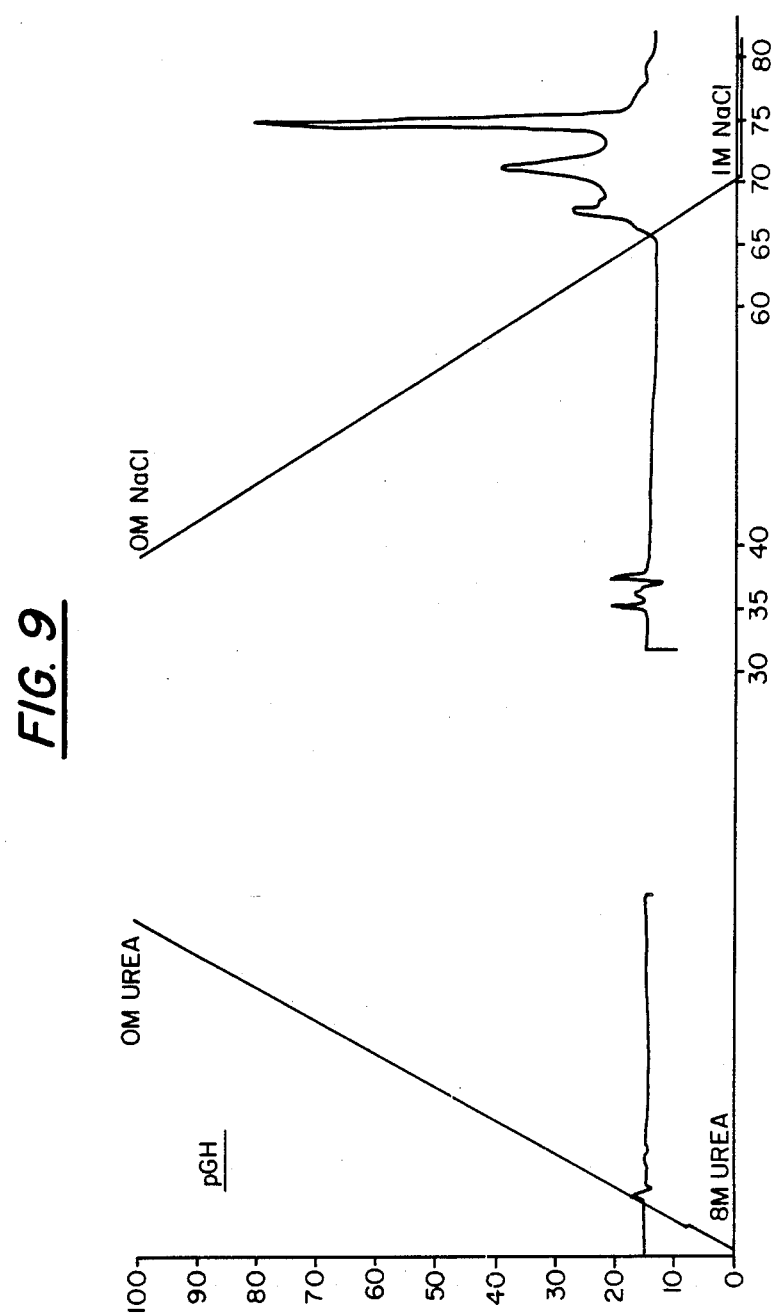
FIG. 9 is a graph showing the elution profile from a Pharmacia Mono Q FTLC column loaded with porcine growth hormone monitored at 280 nm.

FIG. 9 shows the elution profile from the Pharmacia Mono Q FPLC column monitored at 280 nm.

Fractions collected from the column as described above in the legend to FIG. 6 were analysed as described in Example 2.

I claim:

1. A process for the production of a protein in native form, in which a solution of the denatured protein is contacted with a solid phase and the denatured protein is reversibly bound to the solid phase, characterised in that the bound protein is renatured by progressively reducing with time the concentration of denaturing agent in the solvent in contact with the solid phase, and the renatured protein is recovered from the solid phase in native form.

2. A process according to claim 1 where the solid phase is treated with a solvent gradient in which the composition varies from one in which the solvent initially presents a denaturing environment to one in which the solvent presents a natural environment to the protein.

3. A process according to claim 2 wherein the solvent gradient is a linear gradient.

4. A process according to claim 1 where the denaturing agent is urea.

5. A process according to claim 3 wherein the solvent gradient is a urea gradient which varies from an initial urea concentration of 8M to a final concentration of 0M over a period of 60 minutes.

6. A process according to claim 1 where the protein is a protein produced by recombinant DNA biotechnology in which an insoluble form of the protein is produced by host cells transformed with a vector including a gene coding for the protein.

7. A process according to claim 1 where the solvent which is contacted with the solid phase contains one or more components selected from denaturing agent, cofactors, disulphide forming and breaking reagents and salts.

8. A process according to claim 7 where the solvent which is contacted with the solid phase contains urea and dithiothreitol.

9. A process according to claim 1 where the solid phase adsorbent is an ion-exchange resin.

10. A process according to claim 1 where the solid phase adsorbent is cellulose.

11. A process according to claim 1 where the solid phase adsorbent is an agarose or similar material.

12. A process according to claim 1 where the renatured protein is recovered from an ion-exchange column by elution with a salt solution.

* * * * *